United States Patent [19]

Mohan

[11] 4,074,046
[45] Feb. 14, 1978

[54] PROCESS FOR AZOLES (RING CLOSURE OF NITRO COMPOUNDS)

[75] Inventor: Arthur Gaudens Mohan, Branchburg Township, Somerset County, N.J.

[73] Assignee: American Cyanamid Company, Stamford, Conn.

[21] Appl. No.: 731,978

[22] Filed: Oct. 14, 1976

Related U.S. Application Data

[63] Continuation-in-part of Ser. No. 435,377, Jan. 21, 1974, abandoned, which is a continuation of Ser. No. 241,814, April 6, 1972, abandoned, which is a continuation of Ser. No. 846,282, July 30, 1969, abandoned.

[51] Int. Cl.$^2$ ............... C07D 413/06; C07D 263/54; C07D 277/60
[52] U.S. Cl. ............................ 542/439; 260/304 R; 260/307 D; 542/442; 542/455; 542/466; 542/474; 542/476; 548/305; 548/325
[58] Field of Search ............... 260/304, 307 D, 309.2; 542/439, 442, 455, 466, 474, 476

[56] References Cited

U.S. PATENT DOCUMENTS 3,461,149  8/1969  Hardy et al. .................. 260/453

FOREIGN PATENT DOCUMENTS 1,232,922  1/1967  Germany.

OTHER PUBLICATIONS

Elderfield, Heterocyclic Compounds, vol. 5, (1957), J. Wiley & Sons, N. Y., N. Y., pp. 507, 508.
Hardy et al. Tet. Letters 11 (1967) pp. 961–962.
Noller, Chem. of Organic Comps., W. B. Saunders Co., Philadelphia, 3rd ed. 1966, p. 42.

*Primary Examiner*—Arthur P. Demers
*Attorney, Agent, or Firm*—Charles J. Fickey

[57] ABSTRACT

Process for preparing known classes of 2-substituted azoles (I) and N-acylazolinones (II) by reacting carbon monoxide at elevated temperature and pressure in the presence of a cocatalyst composition, of which 5% palladium on carbon with a Lewis acid such as ferric chloride is representative, with a nitrogenous compound (III):

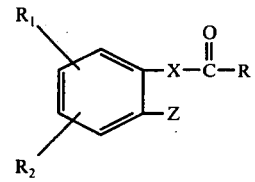

to form the products (usually in admixture):

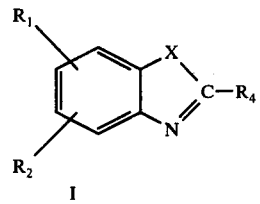 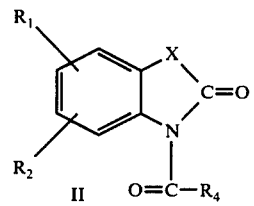

where R is alkyl, alkenyl, aralkyl, aryl, styrl or

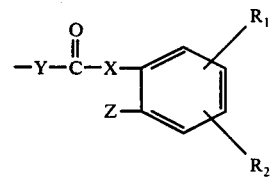

$R_1$ and $R_2$ are hydrogen, alkyl, alkoxy, aryl, halo or, when taken together on adjacent carbon atoms, -CH=CH-CH=CH-; $R_4$ may be alkyl, alkenyl, aralkyl, aryl, styryl,

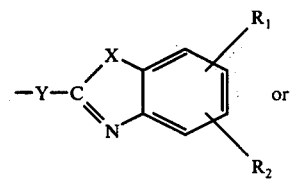 or

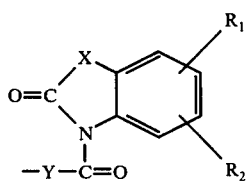

X is oxygen, sulfur or imino, Y is alkylene, alkenylene or arylene; and Z is nitro, azo or azoxy.

6 Claims, No Drawings

PROCESS FOR AZOLES (RING CLOSURE OF NITRO COMPOUNDS)

This is a continuation-in-part of application Ser. No. 435,377, filed Jan. 21, 1974 now abandoned, which was a continuation of application Ser. No. 241,814, filed Apr. 6, 1972, now abandoned, which was a continuation of application Ser. No. 846,282, filed July 30, 1969, now abandoned.

Generally stated, the subject matter of the present invention relates to a new process for preparing organic azole compounds by ring closure. More particularly, it relates to a process for preparing 2-substituted azoles of Formula I and N-acylazolinones of Formula II:

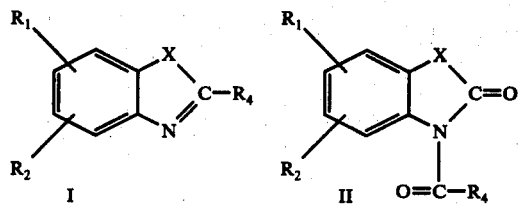

In the above formulas, X is oxygen, sulfur, or imino

$R_4$ is alkyl, alkenyl, aralkyl, aryl, styryl (—CH=CH—C$_6$H$_5$) or, in the case of Formula I,

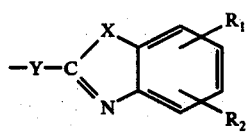

and, in the case of Formula II,

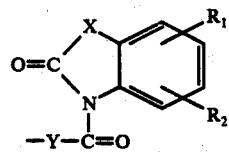

$R_1$ and $R_2$ independently are hydrogen, alkyl, alkoxy, aryl, halo or, when taken together on adjacent carbon atoms, —CH=CH—CH=CH—; $R_3$ is hydrogen, alkyl or aryl; and Y is alkylene, alkenylene or arylene.

The products of Formula I include benzoxazoles and naphthoxazoles (where X is oxygen), benzothiazoles and naphthothiazoles (where X is sulfur) and benzimidazoles and naphthimidazoles (where X is imino). The products of Formula II include N-acyl derivatives of benzoxazolinones and naphthoxazolinones (where X is oxygen), benzothiazolinones and naphthothiazolinones (where X is sulfur) and benzimidazolinones and naphthimidazolinones (where X is imino).

The known methods for preparing compounds of Formula I usually involve cyclization of the corresponding amino compounds (Formula III below where Z is amino), the amino compounds being generated in situ by reduction of the corresponding nitro compound (German Pat. No. 1,232,922). The compounds of Formula II are usually prepared by acylation of the corresponding oxazolinones, thiazolinones and imidazolinones.

It has now been discovered that azole compounds of Formulas I and II can be made by the reaction of nitrogenous compounds of Formula III (below) with carbon monoxide in the presence of a catalyst consisting essentially of a noble metal and a Lewis acid under conditions of superatmospheric pressure and elevated temperature.

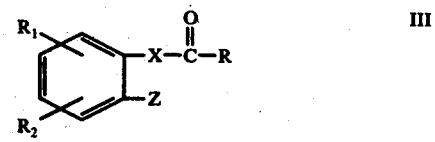

In Formula III, X, $R_1$, $R_2$, $R_3$ and Y have the same meaning as in Formulas I and II; R is alkyl, alkenyl, aralkyl, aryl, styryl or

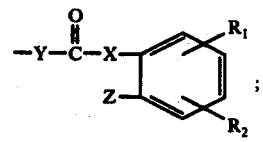

and Z is a nitrogenous substituent selected from nitro, azo and azoxy. Nitro is the preferred nitrogenous group.

The reaction between the nitrogenous compound and carbon monoxide may be carried out in an autoclave or any other high pressure reactor. The nitrogenous compound and catalyst in a solvent, if one is employed, are charged to the reaction vessel, the proper amount of carbon monoxide is added, and the reaction mixture is heated. Sequence of charging is not critical nor are the isolation and purification procedures. Normally, the reaction product mixture is centrifuged or filtered to remove the catalyst, the solvent is evaporated, and the products isolated and purified by crystallization or by vapor phase chromatography.

The compounds of Formula III are acyl derivatives of phenols, thiols and amines. The compounds can be obtained by acylating the phenols, thiols and amines (Formula IV below where $R_1$, $R_2$, X and Z are as defined above) with carboxylic acid, halides or anhydrides in the presence of a base according to well-known procedures. The compounds may also be prepared in situ in the presence of the carbon monoxide.

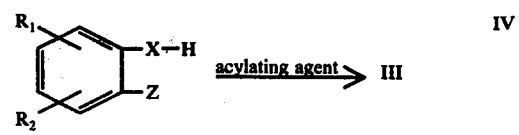

Compounds of Formula IV include phenols and naphthols, such as o-nitrophenol, 5-methoxy-2-nitrophenol, 4-ethoxy-2-nitrophenol, 2-nitro-m-cresol, 6-nitro-m-cresol, 2-nitro-p-cresol, 2-nitro-3,5-xylenol, 4-sec-pentyl-2-nitrophenol, 5-phenyl-2-nitrophenol, 4-chloro-2-nitrophenol, 4-chloro-5-methoxy-2-nitrophenol, 3,6-dichloro-2-nitrophenol, 2,4-diiodo-6-nitrophenol, 4-bromo-2-nitrophenol, 5-chloro-2-nitrophenol, 1-nitro-2-naphthol, 2-nitro-1-naphthol, 2-nitro-4-phenyl-1-naphthol, 2,2'-azodiphenol, 2,2'-azobis(4-chlorophenol), 2,2'-azobis(3,5-dibromophenol), 2,2'-azodi-p- cresol, 2,2'-azobis(6-chloro-p-cresol), 6,6'-azodi-m-cresol, 1,1'-azodi(2-naphthol), and the like; benzenethiols and napthhthalenethiols, such as o-nitrobenzenethiol, 4-chloro-2-nitrobenzenethiol, 4-bromo-2-nitrobenzenethiol, 4,5-dichloro-2-nitrobenzenethiol, 6-nitro-o-toluenethiol, 1-nitro-2-naphthalenethiol, 2-nitro-1-naphthalenethiol, and the like; and anilines and naphthylamines, such as o-nitroaniline, 2-nitro-p-toluidine, 4-tert-butyl-2-nitroaniline, 2-nitro-m-anisidine, N-methyl-o-nitroaniline, 4-bromo-2-nitroaniline, 4,6-dichloro-2-nitroaniline, 2-nitrodiphenylamine, 2-nitro-1-naphthylamine, 1-nitro-2-naphthylamine, 3-nitro-2-naphthylamine, 2,2'-azodianiline, 2,2'-azoxydianiline, and the like.

The carboxylic acid halides and anhydrides which may be used in preparing Formula IV compounds include the halides and anhydrides of aliphatic carboxylic acids, i.e., acids with an alkyl or aralkyl group bonded to the carboxyl group, such as acetic acid, propionic acid, butyric acid, hexanoic acid, lauric acid, myristic acid, stearic acid, acrylic acid, crotonic acid, sorbic acid, oleic acid, succinic acid, fumaric acid, sebacic acid, phenylacetic acid, 1-naphthaleneacrylic acid, cinnamic acid, cyclohexaneacetic acid, and the like; and aromatic carboxylic acids, such as benzoic acid, 3,4-dimethylbenzoic acid, 1-naphthoic acid, 2-naphthoic acid, o-, m- and p-toluic acids, phthalic acid, terephthalic acid, 3,3'-diphenic acid, pyrrole-2-carboxylic acid, and the like.

Representative acyl compounds of Formula III (all known) include o-nitrophenyl acetate, o-nitrophenyl butyrate, o-nitrophenyl isobutyrate, o-nitrophenyl palmitate, o-nitrophenyl stearate, o-nitrophenyl methacrylate, o-nitrophenyl oleate, o-nitrophenyl succinate, o-nitrophenyl benzoate, o-nitrophenyl cinnamate, 1-nitro-2-naphthyl acetate, 2,2'-azobis(phenyl acetate), 2,2'-azobis(phenyl benzoate), 2-nitro-1-naphthyl acetate, N-acetyl-2-nitroaniline (i.e., 2'-nitroacetanilide), N-acetyl-N-methyl-2-nitroaniline, N-acetyl-4-ethyl-2-nitroanilline, N-acetyl-4-butyl-2-nitroaniline, N-acetyl-4-phenyl-2-nitroaniline, N-acetyl-N-phenyl-2-nitroaniline, N-acetyl-4,5-dimethoxy-2-nitroaniline, N-acetyl-5-chloro-2-nitroaniline, N-acetyl-2-nitro-1-naphthylamine, N-acetyl-2-nitro-m-toluidine, N-acetyl-2-nitro-p-anisidine, N-benzoyl-2-nitroaniline, S-(2-nitro-1-naphthyl) thioacetate, S-(o-nitrophenyl) thiobenzoate, 2',2'''-azoxybis(acetanilide), and the like.

Suitable pressure for the process will be within the range of about 40 psig. to 100,000 psig. or higher. The preferred pressure is at least 1,000 psig. The reaction proceeds at temperatures above 60° C., preferably between 150° C. and the temperature of decomposition of either the starting material or the product. Reaction time will depend on reaction temperature and pressure and will generally decrease with increasing temperature and pressure.

A solvent is normally employed to facilitate contact of the catalyst and the reactants. Suitable solvents include anhydrous liquids, such as benzene, toluene, xylene, aliphatic halogenated hydrocarbons, such as 1,1,2-trichloro-1,2,2-trifluoroethane; halogenated aromatic hydrocarbons, such as monochlorobenzene, dichlorobenzene trichlorobenzene; glacial acetic acid, acetonitrile; ethers, such as diethyl ether, dibutyl ether and diphenyl ether; and carboxylic acids, anhydrides or esters, such as acetic acid, acetic anhydride and ethyl acetate; and the like.

The amount of carbon monoxide introduced into the reactor should be sufficient to provide at least three moles of carbon monoxide per nitro or azoxy group, and two moles of carbon monoxide per azo group, and preferably is employed in large excess. The required amount of carbon monoxide and the required super-atmospheric pressure are conveniently and preferably provided by pressurizing the reaction vessel with carbon monoxide after introduction of reactants and catalyst.

The catalyst for the reaction of this invention comprises a noble metal and a Lewis acid as defined in the reference book by Jack Hine, "Physical Organic Chemistry," 1962, McGraw-Hill Book Company, New York. The noble metal may be used either in a metallic or a chemically combined state. It may be employed either with or without a physical support. Among the noble metals which may be employed are platinum, palladium, rhodium osmium silver, gold, iridium, and mercury. Palladium is preferred. Among the chemical forms of these metals which can be used are the oxides, sulfate, nitrates and halides, as for example: platinum oxide, rhodium oxide, platinum chloride, rhodium chloride, platinum, nitrate, platinum sulfate and the corresponding palladium compounds. The noble metals or compounds thereof may be employed singly or in admixture.

The Lewis acid component of the catalyst can be a halide (e.g., an iodide, bromide, chloride or fluoride) of a metal such as tin, titanium, vanadium, molybdenum, gallium, iron, aluminum or copper.

Specific examples of Lewis acids are ferric chloride, ferrous chloride, stannic chloride, stannous chloride, aluminum chloride, titanium tetrachloride, vanadium pentoxide, molybdenum dioxide, aluminum bromide, gallium trichloride, copper tribromide, and cuprous chloride. Additional examples of the salt-type of Lewis acid are listed in the reference book by George A. Olah, "Friedel-Crafts and Related Reactions," Vol. I, 1963, Interscience Publishers, New York. Bronsted acid-type of Lewis acids may be used. An example is anhydrous hydrogen chloride. Other Bronsted acids may be used provided they do not react with the starting materials or the products. The preferred Lewis acids are the chlorides of iron and the Lewis acids may be employed singly or in admixture.

The physical form of the catalyst can be varied as desired. The metal can be self-supported or deposited upon a support which disperses the metal so as to increase active surface area. Such porous supports include alumina, silica, carbon, barium sulfate, asbestos, bentonite, diatomaceous earth, and the like.

A preferred co-catalytic system consists of 5% palladium supported on carbon and ferric chloride. Other co-catalyst systems comprise $PdCl_2$ and $AlCl_3$; PdO and $AlCl_3$; Rh and $FeCl_3$; Pd and $FeCl_2$; PtO and $FeCl_3$.

The catalyst is used in an amount effective to form the desired products. This amount depends to some extent on reaction pressure and temperature, sensitivity of the starting materials towards decomposition, and other process conditions. A useful range is from about $10^{-5}$ to 0.5 gram-atom of noble metal and from about $5 \times 10^{-4}$ to 0.15 mol of Lewis acid per nitrogen atom in the reactant, preferably about 0.02–0.001 mol of Lewis acid and 0.05 to 0.005 gram-atom of noble metal per nitrogen atom.

A feature of the present invention is the discovery that the product ratio can be controlled by choice of solvent. Thus, it has been found that products of Formula I are usually favored when polar solvents are employed and products of Formula II are usually favored when non-polar solvents are utilized. Preferred polar solvents include carboxylic acids or anhydrides such as acetic acid and acetic anhydride, ethers such as diethyl ether and diphenyl ether, nitriles such as acetonitrile and benzonitrile, and certain halogenated hydrocarbons such as chlorobenzene and the "Freon" compounds (trichlorotrifluoroethane and the like). Preferred non-polar solvents include the aromatic hydrocarbons such as benzene, toluene and xylene.

Product ratio is also somewhat dependent on the noble metal employed in the catalyst composition, palladium favoring formation of products of Formula I and rhodium favoring formation of products of Formula II. Furthermore, product ratios are dependent to some extent on the amount of the Lewis acid co-catalyst. For example, increased concentration of ferric chloride favors formation of products of Formula I.

EXAMPLE 1

2-Methylbenzoxazole

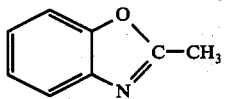

An autoclave is charged with 18.1 g. o-nitrophenyl acetate, 2.50 g. 5% palladium-on-carbon, 0.50 g. ferric chloride 25 ml. acetic anhydride and 75 ml. acetic acid, purged with nitrogen, pressurized to 5,000 psig. with carbon monoxide, and heated at 190° C. for 5 hours. Analysis of the reaction mixture by vapor phase chromatography indicates complete conversion of the o-nitrophenyl acetate to 2-methylbenzoxazole. The catalyst is separated by filtration and washed with acetone. The solvents are evaporated and the residual oil is dissolved in ether and the solution is washed with aqueous sodium bicarbonate and water. After evaporation of the ether, the crude product is distilled to obtain 2-methylbenzoxazole, b.p.$_{30 mm}$ 102°–110° C. The product is identical with an authentic sample of 2-methylbenzoxazole by vapor phase chromatography and infrared spectrum.

When the above procedure is followed substituting equivalent amounts of o-nitrophenyl butyrate, o-nitrophenyl methacrylate, o-nitrophenyl palmitate, o-nitrohenyl cinnamate, or 1-nitro-2-naphthyl acetate, for the o-nitrophenyl acetate, the following products are obtained; 2-propylbenzoxazole, 2-(1-methylvinyl)benzoxazole, 2-pentadecylbenzoxazole, 2-styrylbenzoxazole and 2-methylnaphth-[1,2-d]-oxazole, respectively.

When the above procedure is repeated substituting equivalent amounts of 2,2'-azobis(phenyl acetate) or 2,2'-azobis(4-chlorophenyl acetate) for the o-nitrophenyl acetate, 2-methylbenzoxazole and 2-methyl-5-chlorobenzoxazole, respectively, are obtained.

EXAMPLE 2

2-Phenylbenzoxazole  3-Benzoyl-2-benzoxazolinone

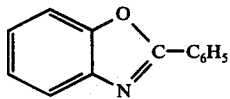 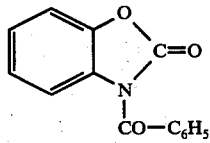

An autoclave is charged with 2.43 g. o-nitrophenyl benzoate, 0.50 g. 5% palladium-on-carbon, 0.25 g. ferric chloride and 20 ml. of acetonitrile, purged with nitrogen, pressurized to 5,000 psig. with carbon monoxide, and heated at 190° C. for 6 hours. Analysis of the reaction mixture by vapor phase chromatography shows that the major component (87%) is 2-phenylbenzoxazole and a minor component is 3-benzoyl-2-benzoxazolinone. The catalyst is removed and the solvent is evaporated. Chromatography of the residual oil on alumina yields 2-phenylbenzoxazole, melting point 100°–102° C., identical with an authentic sample by mixed melting point and infrared spectrum.

When the above procedure is followed substituting an equivalent amount of 2,2'-azobis(5-chlorophenyl benzoate) for the o-nitrophenyl benzoate, 6-chloro-2-phenylbenzoxazole is obtained.

When the above procedure is repeated substituting 5% rhodium-on-carbon for the palladium-on-carbon, 2-phenylbenzoxazole and 3-benzoyl-2-benzoxazolinone are obtained in 1.0/2.5 weight ratio (29% with 71% respectively).

When the above procedure is repeated using benzene as the solvent, 3-benzoyl-2-benzoxazolinone is obtained as the major product.

EXAMPLE 3

2,2'-(Vinylene)bis(5-methylbenzoxazole)

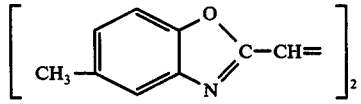

An autoclave is charged with 1.93 g. bis(2-nitro-p-tolyl) furmarate, 0.50 g. 5% palladium-on-carbon, 0.08 g. ferric chloride and 15 ml. acetonitrile, purged with nitrogen, pressurized to 7,500 psig. with carbon monoxide and heated at 190° C. for 8 hours. Analysis of the reaction mixture by thin layer chromatography shows that the major product is 2,2'-(vinylene)bis(5-methylbenzoxazole).

Similar results are obtained when ferrous chloride is substituted for the ferric chloride. When the above procedure is repeated substituting an equivalent amount of bis(2-nitrophenyl) succinate for the bis(2-nitro-p-tolyl) fumarate, 2,2'-(ethylene)-bis(benzoxazole) is obtained.

EXAMPLE 4

2,5,6-Trimethylbenzoxazole

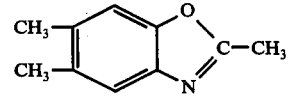

An autoclave is charged with 8.36 g. 6-nitro-3,4-xylenol, 1.25 g. 5% palladium-on-carbon, 0.25 g. ferric chloride, 75 ml. acetic acid, and 25 ml. acetic anhydride, pressurized to 5,000 psig. with carbon monoxide and heated at 120° C. for 2 hours and then at 190° C. for 5 hours. Analysis of the reaction mixture by vapor phase chromatography shows that 2,5,6-trimethylbenzoxazole is the major product.

This example demonstrates the preparation "in situ" of the starting 6-nitro-3,4-xylyl acetate.

EXAMPLE 5

2-Styrylbenzoxazole

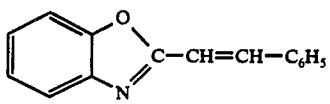

3-Cinnamoyl-2-Benzoxazolinone

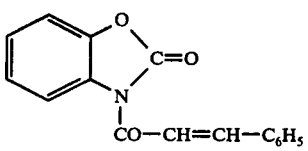

An autoclave is charged with 13.45 g. o-nitrophenyl cinnamate, 2.5 g. 5% palladium-on-carbon, 0.40 g. ferric chloride and 90 ml. anhydrous acetonitrile, pressurized with carbon monoxide to 5000 psig., and heated at 190° C. for 6 hours. After the catalyst is removed by filtration, analysis of the reaction mixture by vapor phase chromatography shows that 2-styrylbenzoxazole is the major product. The 2-styrylbenzoxazole is isolated by chromatography on alumina using benzene as the eluent. After recrystallization from petroleum ether, it melts at 78°–79° C. and is identical with an authentic sample of 2-styrylbenzoxazole by mixed melting point, infrared spectrum and vapor phase chromatography.

When the above procedure is repeated using chlorobenzene as the solvent, 3-cinnamoyl-2-benzoxazolinone and 2-styrylbenzoxazole are obtained in 2.8/1.0 weight ratio (74% with 26% respectively). The 3-cinnamoyl-2-benzoxazolinone is identical with an authentic sample.

EXAMPLE 6

2-Phenylbenzothiazole 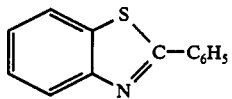   3-Benzoyl-2-benzothiazolinone 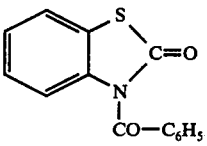

An autoclave is charged with 2.59 g. S-(o-nitrophenyl) thiobenzoate, 0.50 g. 5% palladium-on-carbon, 0.05 g. ferric chloride and 20 ml. benzene, purged with nitrogen, pressurized to 7,500 psig. with carbon monoxide and heated at 195° C. for 6 hours. After the catalyst is removed by filtration, analysis of the mixture by vapor phase chromatography shows that 2-phenylbenzothiazole is the major product. The solvent is evaporated and the residue is washed with saturated aqueous sodium bicarbonate. The 2-phenylbenzothiazole, isolated by chromatography on alumina, melts at 109.5°–112° C. and is identical by infrared spectrum, mixed melting point and vapor phase chromatography with an authentic sample of 2-phenylbenzothiazole. 3-Benzoyl-2-benzothiazolinone is a minor product.

When the above procedure is followed substituting an equivalent amount of S-(2-nitro-1-naphthyl) thioacetate for the S-(o-nitrophenyl) thiobenzoate, the products are 2-methylnaphtho[2,1-d]thiazole and 3-acetyl-2-naphtho[2,1-d]thiazolinone.

EXAMPLE 7

2-Methylbenzimidazole

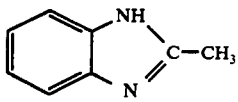

An autoclave is charged with 18.0 g. 2'-nitroacetanilide, 5.0 g. 5% palladium-on-carbon, 0.5 g. ferric chloride and 100 ml. glacial acetic acid, purged with nitrogen, pressurized to 5,000 psig. with carbon monoxide and heated at 190° C. for 6 hours. After the catalyst is removed by filtration and the solvent is evaporated, analysis of the residue by vapor phase chromatography shows that the major product is 2-methylbenzimidazole. The residue is extracted with dilute hydrochloric acid and the extract is neutralized to pH 8 with sodium carbonate solution. A solution of the resulting precipitate in chloroform is filtered to remove inorganic materials and the solent is evaporated. The 2-methylbenzimidazole, after recrystallization from benzene-chloroform, melts at 176°–178° C. and is identical with an authentic sample of 2-methylbenzimidazole by infrared spectrum and mixed melting point.

When the above procedure is repeated substituting an equivalent amount of 4'-ethyl-2'-nitroacetanilide, 4'-phenyl-2'-nitroacetanilide, 5'-chloro-2'-nitroacetanilide, N-methyl-2'-nitroacetanilide, N-phenyl-2'-nitroacetanilide, 2'-nitro-m-acetotoluidide, 2'-nitro-p-acetaniside, 2'-nitrobenzanilido, 4-propoxy-2'-nitrobenzanilido, 2'-nitro-2-naphthanilide or N-(2-nitro-1-naphthyl)acetamide for the 2'-nitroacetanilide, the products are 5-methylbenzimidazole, 5-phenyl-2-methylbenzimidazole, 6-chloro-2-methylbenzimidazole, 1,2-dimethylbenzimidazole, 2-methyl-1-phenylbenzimidazole, 2,4-dimethylbenzimidazole, 5-methoxy-2-methylbenzimidazole, 2-phenylbenzimidazole, 2-(4-propoxyphenyl) benzimidazole, 2-(2-naphthyl) benzimidazole, and 2-methyl-1H-naphth[1,2-d]imidazoke, respectively.

When the above procedure is repeated substituting an equivalent amount of 2,2'-azoxybis(acetanilide) for the 2'-nitroacetanilide, 2-methylbenzimidazole is obtained.

EXAMPLE 8

The following table shows the effect of solvent on product ratios of reactions conducted substantially as described in the preceding examples. It will be noted that the polar solvents favor formation of products of Formula I and the nonpolar solvents favor formation of products of Formula II.

TABLE I

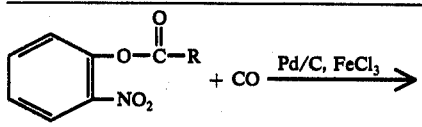

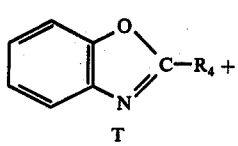

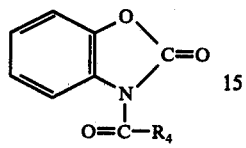

|  |  |  | Product Analysis (VPC) | |
|---|---|---|---|---|
| Ex. | Compound (R=R₄) | Solvent | I | II |
| (a) | —C₆H₅ | Benzene | Trace | Major |
| (b) | —CH=CH—C₆H₅ | Benzene | Trace | Major |
| (c) | —CH₃ | Benzene | Trace | Major |
| (d) | —C₆H₅ | Acetonitrile | 83% | 17% |
| (e) | —CH=CH—C₆H₅ | Acetonitrile | Major | Trace |
| (f) | —CH₃ | Acetonitrile | Major | Nil |
| (g) | —CH=CH—C₆H₅ | Chlorobenzene | 26% | 74% |
| (h) | —CH=CH—C₆H₅ | ClF₂CCCl₂F | 83% | 17% |
| (i) | —CH=CH—C₆H₅ | Benzene[1] | 29% | 71% |
| (j) | —CH₃ | Acetic acid, Acetic anhydride | Major |  |

[1]FeCl₂ was co-catalyst in place of FeCl₃

The products of this invention have a wide variety of uses and may be employed therein in known or obvious ways. For example, the 2-substituted azoles (formula I) can be employed as optical brighteners or bleaches, or can be used as intermediates in the manufacture of such products. As optical brighteners they can be used on a variety of textile materials, both natural and synthetic, such as cotton, wool, silk, nylon, polyesters, and the like. Such uses and how to use are set forth, for example, in Kirk-Othmer: "Encyclopedia of Chemical Technology," Second Edition, volume 3, page 737; U.S. Pat. Nos. 2,733,869, 2,793,192, 3,120,520 and 3,274,184; and Belgium Pat. No. 719,584. The N-acylazolinones (formula II) are antimicrobials or would be expected to exhibit antimicrobial activity and may be employed in known or obvious ways for these effects. For example, the N-benzoyl derivatives of the formula II 2-benzoxazolinones are bactericides and fungicides, Chem. Abstracts 66, P105,000r, and the hydrazone and oxime of N-acetyl-2-benzoxazolinone are tuberculostatic, Chem. Abstracts 49, 9160a.

The foregoing examples are intended as specific illustration of the invention but not necessarily to limit it.

I claim:

1. A process for preparing 2-substituted azoles having the formulas:

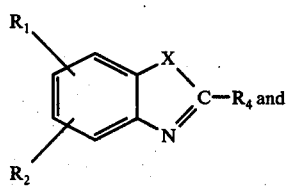

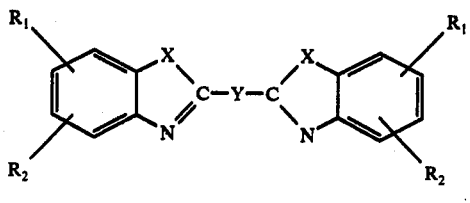

and N-acylazolinones having the formula:

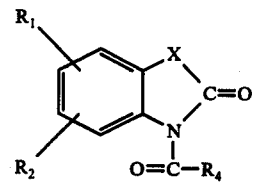

which comprises reacting a nitrogenous compound of the formula:

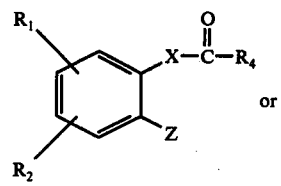

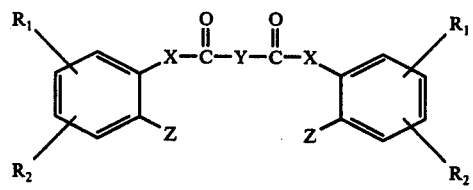

wherein X is oxygen, or sulfur;

R₄ is selected from the group consisting of alkyl C₁-C₁₅, alkenyl C₂-C₄, aryl C₆-C₁₀, or aralkynyl C₈-C₁₀;

R₁ and R₂ are independently hydrogen, alkyl C₁-C₄ and halo, or when taken together on adjacent carbon atoms, -CH=CH-CH=CH-;

Y is alkenylene; and

Z is nitro, azo, or azoxy; with carbon monoxide in the presence of a polar or non-polar solvent for the nitrogenous compound and a co-catalyst composition consisting essentially of about $10^{-5}$ to 0.5 gram-atom palladium or rhodium and about 5 × $10^{-4}$ to 0.15 mol of iron halide per mol of nitrogen atom, at a temperature of above 60° C. but below the decomposition temperature of said nitrogenous compound and a pressure of about 40 psig to 100,000 psig.

2. The process according to claim 1 wherein R₁ and R₂ are methyl.

3. The process according to claim 1 wherein the reaction is carried out in the presence of a polar or nonpolar solvent for the nitrogenous compound.

4. The process according to claim 1 wherein the solvent is benzene.

5. The process according to claim 1 wherein the solvent is acetonitrile.

6. The process according to claim 1 wherein the solvent is a mixture of acetic acid and acetic anhydride.

* * * * *